(12) United States Patent
Nair et al.

(10) Patent No.: US 8,808,183 B2
(45) Date of Patent: *Aug. 19, 2014

(54) SYSTEM AND METHOD FOR DETERMINING A TRANSFER FUNCTION

(75) Inventors: Anuja Nair, Copley, OH (US); David Geoffrey Vince, Avon Lake, OH (US); Jon D. Klingensmith, Shaker Heights, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 613 days.

This patent is subject to a terminal disclaimer.

(21) Appl. No.: 12/878,770

(22) Filed: Sep. 9, 2010

(65) Prior Publication Data

US 2011/0087101 A1 Apr. 14, 2011

Related U.S. Application Data

(63) Continuation of application No. 10/758,477, filed on Jan. 14, 2004, now Pat. No. 7,874,990.

(51) Int. Cl.
*A61B 8/00* (2006.01)
(52) U.S. Cl.
USPC ........... 600/437; 600/443; 600/447; 600/441; 600/442
(58) Field of Classification Search
None
See application file for complete search history.

(56) References Cited

U.S. PATENT DOCUMENTS

| | | | | |
|---|---|---|---|---|
| 5,445,155 | A | * | 8/1995 | Sieben .......................... 600/443 |
| 6,038,468 | A | * | 3/2000 | Rex .............................. 600/424 |
| 6,200,268 | B1 | * | 3/2001 | Vince et al. ................... 600/443 |

* cited by examiner

*Primary Examiner* — Unsu Jung
*Assistant Examiner* — Joel Lamprecht
(74) *Attorney, Agent, or Firm* — Haynes and Boone, LLP

(57) ABSTRACT

A system and method is provided for using ultrasound data backscattered from vascular tissue to estimate the transfer function of a catheter (including components attached thereto—e.g., IVUS console, transducer, etc.). Specifically, in accordance with a first embodiment of the present invention, a computing device is electrically connected to a catheter and used to acquire RF backscattered data from a vascular structure (e.g., a blood vessel, etc.). The backscattered ultrasound data is then used, together with an algorithm, to estimate the transfer function. The transfer function can then be used (at least in a preferred embodiment) to calculate response data for the vascular tissue (i.e., the tissue component of the backscattered ultrasound data). In a second embodiment of the present invention, an IVUS console is electrically connected to a catheter and a computing device and is used to acquire RF backscattered data from a vascular structure. The backscattered data is then transmitted to the computing device, where it is used to estimate the catheter's transfer function and to calculate response data for the vascular tissue. The response data and histology data are then used to characterize at least a portion of the vascular tissue (e.g., identify tissue type, etc.).

26 Claims, 4 Drawing Sheets

US 8,808,183 B2

SYSTEM AND METHOD FOR DETERMINING A TRANSFER FUNCTION

CROSS-REFERENCE TO RELATED APPLICATION

This application is a continuation application of U.S. patent application Ser. No. 10/758,477, filed Jan. 14, 2004, (now U.S. Pat. No. 7,874,990) the disclosure of which is hereby incorporated by reference in its entirety.

BACKGROUND OF THE INVENTION

1. Field of the Invention

The present invention relates to the intravascular-ultrasound (IVUS) arts, or more particularly, to a system and method of using ultrasound data backscattered from vascular tissue to estimate the transfer function of a catheter (including components attached thereto—e.g., IVUS console, transducer, etc.).

2. Description of Related Art

Ultrasound imaging of the coronary vessels of a patient can provide physicians with valuable information. For example, such an image may show the extent of a stenosis in a patient, reveal progression of disease, determine the vulnerability of the atherosclerotic plaque for causing myocardial infarction, help determine whether procedures such as angioplasty or atherectomy are indicated, or whether more invasive procedures are warranted.

In a typical ultrasound imaging system, a catheter (including an ultrasonic transducer attached thereto) is carefully maneuvered through a patient's blood vessel to a point of interest. Acoustic signals are then transmitted and echoes (or backscatter) of the acoustic signals are received. The backscattered ultrasound data ("backscattered data") can be used to identify the type or density of the tissue being scanned. When the echoes (or multiple sets thereof) are received, acoustic lines are processed, building up a sector-shaped image of the blood vessel. After the backscattered data is collected, an image of the blood vessel (i.e., an intravascular-ultrasound (IVUS) image) is reconstructed using well-known techniques. This image is then visually analyzed by a cardiologist to assess the vessel components and plaque content.

One drawback of such a system, however, is that the ultrasound data backscattered from the vascular tissue may not accurately represent the tissue. This is because the backscattered data may further include a noise component and a catheter component. For example, with respect to the latter, manufacturing tolerances can cause different catheters (or devices connected thereto—e.g., IVUS console, transducer, etc.) to operate differently (e.g., at slightly different frequencies, etc.), thus producing different results. This influence on the system is referred to herein as the "transfer function."

Traditionally, the transfer function has been determined (i) with the catheter outside the patient and (ii) through the use of a perfect reflector (e.g., plexiglass, etc.). Specifically, the catheter would be positioned near the reflector and used to transmit ultrasound data toward the reflector and to receive ultrasound data backscattered from the reflector. Because the reflector backscatters all (or substantially all) of the data transmitted, the catheter's transfer function can then be computed. This is because the backscattered data (B) is equal to the transmitted data (T) as modified by the transfer function (H) (i.e., B=TH). Drawbacks of such a system, however, are that the transfer function cannot be computed in real-time (e.g., while data backscattered from vascular tissue is being acquired, etc.) and requires the use of additional components (e.g., a perfect reflector, etc.). Thus, it would be advantageous to have a system and method for determining the transfer function of a catheter that overcomes at least one of these drawbacks.

SUMMARY OF THE INVENTION

The present invention provides a system and method of using ultrasound data backscattered from vascular tissue ("backscattered data") to estimate the transfer function of a catheter, which can then be used to calculate response data for the vascular tissue. Embodiments of the present invention operate in accordance with a catheter having at least one transducer, a computing device, and a transfer-function application. Specifically, in accordance with a first embodiment of the present invention, the computing device is electrically connected to the catheter and used to acquire RF backscattered data from a vascular structure (e.g., a blood vessel, etc.). This is accomplished by maneuvering the transducer portion of the catheter through the vascular structure to a point of interest and pulsing the transducer to acquire echoes, or data backscattered from vascular tissue. The transfer-function application is then adapted to use the backscattered data and an algorithm to estimate the transfer function of the catheter. The transfer function can then be used (at least in a preferred embodiment) to calculate response data for the vascular tissue (i.e., the "pure" tissue component of the backscattered data).

In one embodiment of the present invention, the algorithm is an iterative algorithm that is time-invariant over small intervals. In another embodiment of the present invention, the algorithm executes multiple underlying equations (e.g., an error-criteria equation, a least-squares-fit equation, etc.) and/or rely on certain selected or pre-specified parameters (e.g., a scale parameter, a shift parameter, a sign parameter, etc.). In another embodiment of the present invention, the algorithm may further be used to estimate response data for the vascular tissue. Thus, for example, execution of the algorithm may produce estimated values for both the transfer function and the response data.

The transfer function's influence on the backscattered ultrasound data can be represented with the frequency domain equation $Z(\omega)=X(\omega)H(\omega)+E(\omega)$, where Z is the backscattered data, X is the response data for vascular tissue, H is the transfer function, and E is the noise (or error) component of the backscattered data. In one embodiment of the present invention, the transfer function (H) and the backscattered data (Z) are used to calculate the response data (X) (e.g., X=Z/H). In another embodiment of the present invention, the transfer function (H), the backscattered data (Z), and the estimated response data ($X_{est}$) are used to calculate the response data (X). For example, the transfer function (H) and the backscattered data (Z) could be used to calculate response data ($X_{cal}$) (e.g., $X_{cal}$=Z/H), and the calculated response data ($X_{cal}$) and the estimated response data ($X_{est}$) could be used to calculate the response data (X) (e.g., final response data where X is a function of $X_{cal}$ and $X_{est}$). In another embodiment of the present invention, the estimated response data ($X_{est}$), alone (i.e., without the calculated response data ($X_{cal}$)), is used to calculate the response data (X) (e.g., $X_{est}$=X, etc.) In another embodiment of the present invention, the transfer-function application is further adapted to filter out the noise component (E) of the backscattered data (Z).

In a second embodiment of the present invention, an IVUS console is electrically connected to a catheter having at least one transducer and a computing device, wherein the computing device includes a transfer-function application, a characterization application, and a database. Specifically, the IVUS console is used to acquire RF backscattered data from a vascular structure (e.g., via the catheter). The backscattered data is then transmitted to the computing device, where it is used by the transfer-function application to estimate the transfer function (H) and to calculate the response data (X) (as previously discussed). Parameters of the response data (X) are then compared (i.e., by the characterization application) with histology data stored in the database in an effort to characterize the vascular tissue (e.g., identify tissue type, etc.).

Specifically, prior to the calculation of response data (X), parameters are stored in the database and linked to characterization data (tissue types, etc.). After the response data (X) is calculated, the characterization application is used to identify at least one parameter associated (either directly or indirectly) with the response data (X). The identified parameters are then compared to the parameters stored in the database (i.e., histology data). If a match (either exactly or substantially) is found, the related region (e.g., vascular tissue or a portion thereof) is correlated to the tissue type (or characterization) stored in the database (e.g., as linked to the matching parameter(s)). In another embodiment of the present invention, the characterization application is further adapted to display a reconstructed image of at least a portion of the interrogated vascular structure on a display (e.g., using gray-scales, colors, etc.).

A more complete understanding of the system and method of using ultrasound data backscattered from vascular tissue to estimate the transfer function of a catheter will be afforded to those skilled in the art, as well as a realization of additional advantages and objects thereof, by a consideration of the following detailed description of preferred embodiments. Reference will be made to the appended sheets of drawings which will first be described briefly.

DETAILED DESCRIPTION OF THE PREFERRED EMBODIMENT

Preferred embodiments of the present invention operate in accordance with a catheter having at least one transducer, a computing device, and a transfer-function application operating thereon. In the detailed description that follows, like element numerals are used to describe like elements illustrated in one or more figures.

Figure 1:
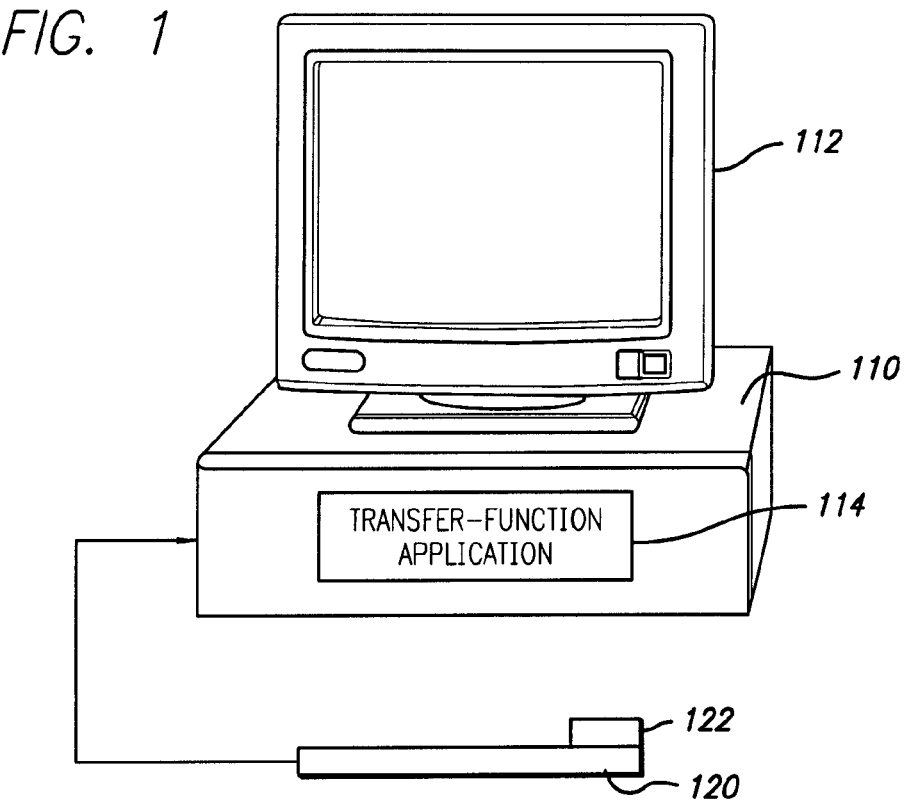
FIG. 1 illustrates an intravascular-ultrasound (IVUS) data-acquisition system in accordance with one embodiment of the present invention, including a computing device and a catheter having a transducer.
Figure 2A:
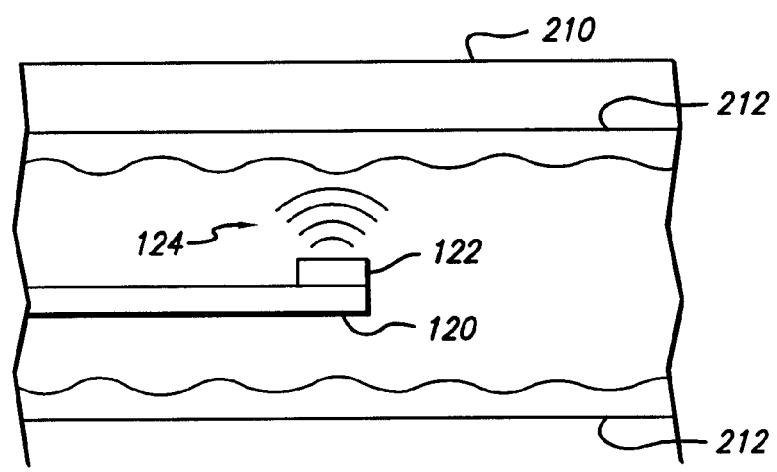
FIG. 2A illustrates a catheter and a transducer operating inside a vascular structure.

FIG. 1 illustrates an intravascular-ultrasound (IVUS) data-acquisition system operating in accordance with a first embodiment of the present invention. In this embodiment, a computing device 110 is electrically connected to a catheter 120 and used to acquire RF backscattered data from a vascular structure (e.g., a blood vessel, etc.). Specifically, as shown in FIG. 2A, the transducer 122 is attached to the end of the catheter 120 and maneuvered through a vascular structure 212 of a patient 210 to a point of interest. The transducer 122 is then pulsed (see e.g., 124) to acquire echoes or backscattered data reflected from the tissue of the vascular structure (see FIG. 2C). Because different types and densities of tissue absorb and reflect ultrasound data differently, the reflected data (i.e., backscattered data) can be used to image the vascular object. In other words, the backscattered data can be used (e.g., by the computing device 110) to create an image of the vascular tissue (e.g., an IVUS image, a tissue-characterization image, etc.). Exemplary images can be seen in FIGS. 4 and 5 of U.S. Pat. No. 6,200,268, issued on Mar. 13, 2001, and in FIGS. 2 and 5 of patent application Ser. No. 10/647,971, filed on Aug. 25, 2003 and claiming priority to Provisional Application Nos. 60/406,254, 60/406,148, and 60/406,183; collectively filed on Aug. 26, 2002; all of which are incorporated herein, in their entireties, by reference.

In another embodiment of the present invention, the computing device 110 further includes a display 112 (e.g., to display the aforementioned image). It should be appreciated that the computing devices depicted herein (i.e., 110 and 330) include, but are not limited to, personal computers, mainframe computers, PDAs, and all other computing devices, including medical (e.g., ultrasound devices, thermographic devices, optical devices, MRI devices, etc.) and non-medical devices, generally known to those skilled in the art. It should also be appreciated that the term "catheter" is used herein in its broad sense, encompassing both the catheter and components attached thereto (e.g., IVUS console, transducer(s), etc.). Thus, for example, while the specification may state that the catheter transmits an ultrasound signal, those skilled in the art will realize that it is actually the transducer portion of the catheter that actually transmits the ultrasound signal. Similarly, while the specification refers to estimating the catheter's transfer function, those skilled in the art will realize that such an estimation further includes the transfer function of components attached thereto (e.g., transducer, IVUS console, etc.). It should further be appreciated that the catheters depicted herein (i.e., 120 and 320) are not limited to any particular type, and include all catheters generally known to those skilled in the art. Thus, for example, a catheter having a single transducer (e.g., adapted for rotation) or an array of transducers (e.g., circumferentially positioned around the catheter) is within the spirit and scope of the present invention.

Referring back to FIG. 1, the IVUS data-acquisition system further includes a transfer-function application 114 that is adapted to use the backscattered data and an algorithm to estimate the transfer function of the catheter 120. To better understand this feature, the transfer function's relationship to the backscattered data will now be discussed.

The transfer function's influence on the backscattered data can be represented, for example, by the frequency domain equation $Z(\omega)=X(\omega)H(\omega)+E(\omega)$, where Z is the backscattered data, X is the "pure" tissue component of the backscattered data (i.e., response data for vascular tissue), H is the catheter component of the backscattered data (i.e., the transfer function), and E is the noise (or error) component of the backscattered data. Thus, once the noise component (E) is filtered out and the transfer function (H) is estimated, the response data for vascular tissue (X) can be determined by dividing the backscattered data (Z) by the transfer function (H) (i.e., X=Z/H).

In a preferred embodiment of the present invention, the transfer function is estimated using (i) backscattered data and (ii) an algorithm. It should be appreciated, however, that the present invention is not limited to any particular algorithm. Thus, any algorithm that uses backscattered data to estimate the transfer function of a catheter is within the spirit and scope of the present invention.

In one embodiment of the present invention, however, the algorithm is iterative and time-invariant over small intervals. For example, the frequency domain equation: $Z(\omega)=X(\omega)H(\omega)+E(\omega)$ can be rewritten in the time domain, yielding the following equation:

$$z[n] = \sum_k x[n-k] * h[k] + e[n]$$

Figure 2B:
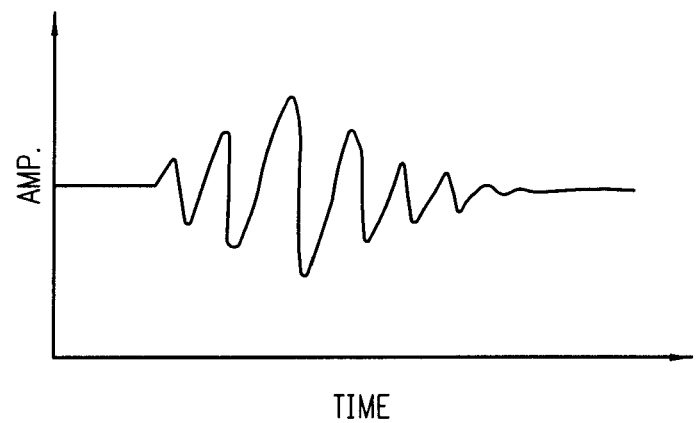
FIG. 2B illustrates exemplary ultrasound data transmitted from a transducer portion of a catheter.
Figure 2C:
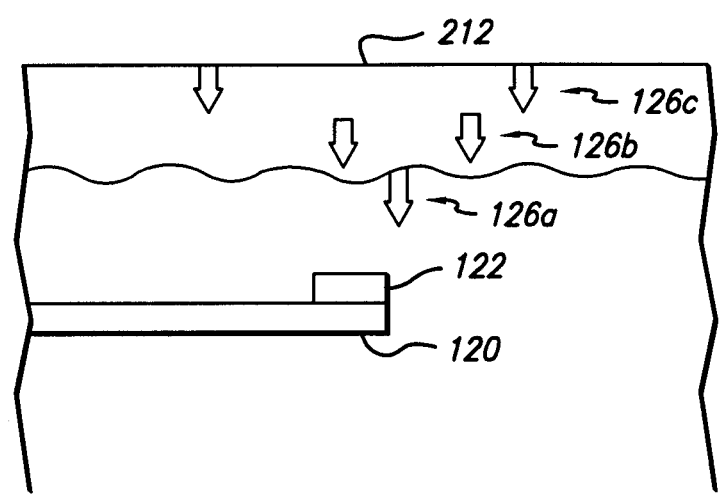
FIG. 2C illustrates exemplary ultrasound data backscattered from vascular tissue.
Figure 2D:
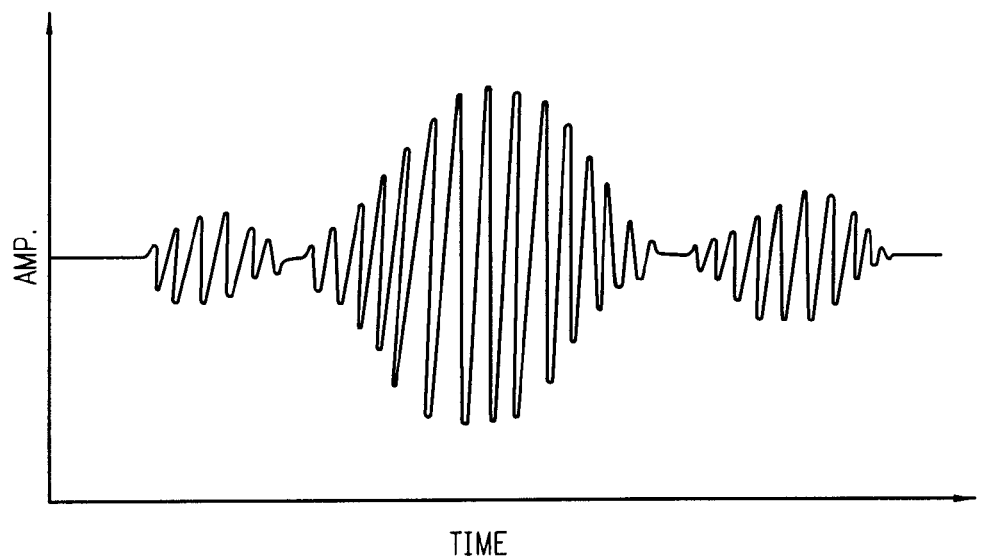
FIG. 2D illustrates exemplary ultrasound data (e.g., as backscattered from vascular tissue) received by a transducer portion of a catheter.

The backscattered ultrasound data, however, is generally backscattered at varying times (i.e., time-variant). This concept is illustrated in FIGS. 2A-2D. Specifically, FIG. 2A illustrates the use of a catheter 120 to transmit an ultrasound signal (or pulse) 124 toward vascular tissue. An exemplary ultrasound signal (e.g., like the one transmitted in FIG. 2A) is illustrated in FIG. 2B. FIG. 2C illustrates that the backscattered data is time-variant. This is because different types and densities of tissue absorb and reflect ultrasound data differently. For example, a first portion of backscattered data 126a might be represent an inner portion of vascular tissue, a second portion of backscattered data 126b might be represent a middle portion of vascular tissue, and a third portion of backscattered data 126c might be represent an outer portion of the vascular tissue. An exemplary pulse of backscattered data (e.g., like the one backscattered in FIG. 2C) is illustrated in FIG. 2D.

Thus, if the time domain equation (depicted above) is then modified using a recursive algorithm via an iterative window maximization method (i.e., to produce a time-variant equation), the aforementioned equation can be rewritten as follows:

$$z[n] = \sum_{k=0}^{K} x[n-k] h[k, n-k] + e[n]$$

If it is then assumed that the noise component is zero mean, Gaussian, white noise and the transfer function is time-invariant over small intervals, the equation becomes:

$$Z = \sum_{i=1}^{I} X_i H_i + e$$

Through the use of this equation, an estimate of H can be determined. One method of estimating H is to search for an estimation of X that minimizes certain error criteria (e.g., the difference between observed data and a fitted model, etc.). Once X is estimated ($X_{est}$), a least-squares-fit algorithm can be used to estimate H. In another embodiment of the present invention, the algorithm further considers certain parameters that are either selected and/or pre-specified. For example, a "scale" parameter could be pre-specified to be energy units, a "shift" parameter could be selected from the backscattered data by estimating the position of the largest sample thereof, a "sign" parameter could be selected from the backscattered data by estimating the sign of the largest sample thereof, etc.

It should be appreciated that while FIG. 1 depicts the transfer-function application 114 being executed within the computing device 110, the present invention is not so limited. Thus, for example, storing and/or executing at least a portion of the transfer-function application within another device (not shown in FIG. 1) is within the spirit and scope of the present invention. It should further be appreciated that while the transfer-function application is used to estimate the transfer function, it may also be used to perform other functions (e.g., filtering out noise (E), etc.).

In one embodiment of the present invention, the transfer function is estimated more than once during the acquisition of intravascular-ultrasound (IVUS) data. Specifically, the acquisition of IVUS data typically includes (i) maneuvering a catheter through a vascular structure (e.g., a blood vessel) of a patient and (ii) acquiring IVUS data while the catheter is being moved through the structure (e.g., pulled back through the structure). However, because the transfer function may change over time (e.g., due to the degradation of components associated thereto, etc.), it may be advantageous to estimate (or re-estimate) the transfer function at different times and/or locations. For similar reasons, in another embodiment of the present invention, the transfer function is estimated continuously (or substantially continuously) for at least a portion of the time that the catheter is within a particular vascular structure.

In a preferred embodiment of the present invention, the transfer function (H) and the backscattered data (Z) are used to calculate the response data (X) (e.g., X=Z/H). In another embodiment of the present invention, the transfer function (H), the backscattered data (Z), and the estimated response data ($X_{est}$) are used to calculate the response data (X). For example, the transfer function (H) and the backscattered data (Z) could be used to calculate the response data ($X_{cal}$) (e.g., $X_{cal}$=Z/H) and the calculated response data NO and the estimated response data ($X_{est}$) could be used to calculate the response data for vascular tissue (X) (e.g., X is a function of $X_{cal}$ and $X_{est}$). In another embodiment of the present invention, the estimated response data ($X_{est}$), alone (i.e., without the calculated response data ($X_{cal}$), is used to calculate the response data (X) (e.g., $X_{est}$=X, etc.).

Figure 3:
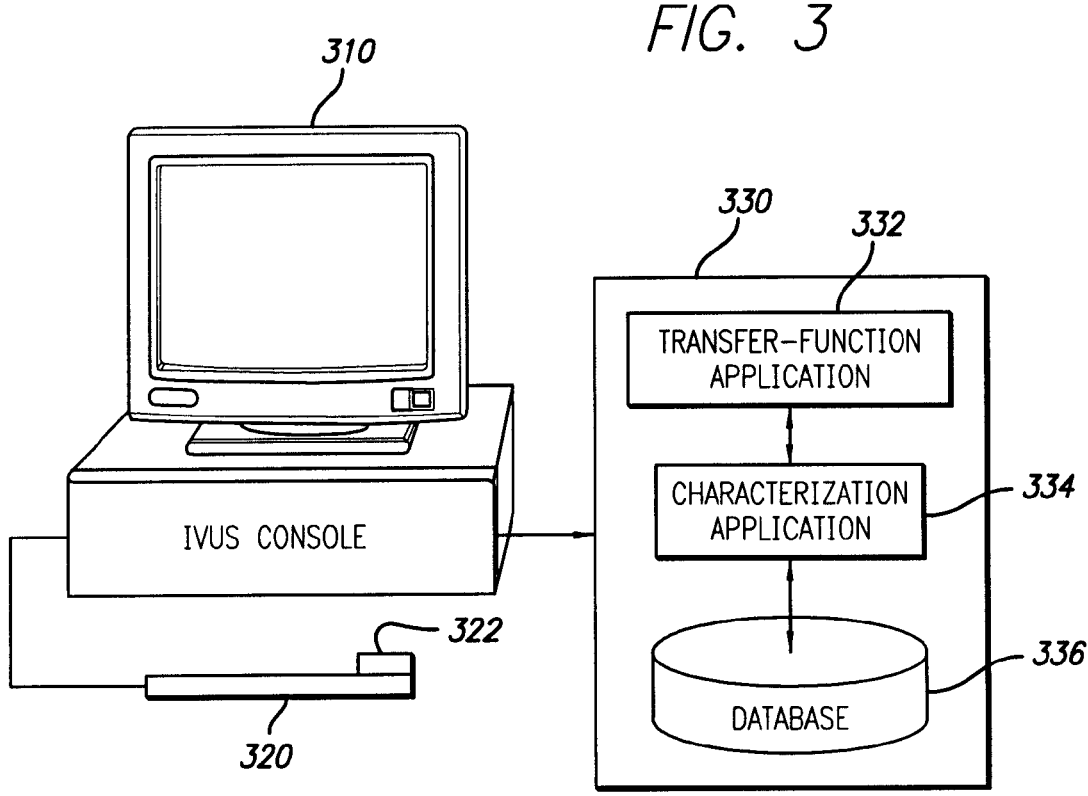
FIG. 3 illustrates a vascular-tissue-characterization system in accordance with one embodiment of the present invention, including an intravascular-ultrasound (IVUS) console, a catheter having a transducer, and a computing device.

FIG. 3 illustrates a vascular-tissue-characterization system operating in accordance with a second embodiment of the present invention. In this embodiment, an IVUS console 310 is electrically connected to a catheter 320 and a computing device 330, wherein the computing device 330 includes at least a transfer-function application 332, a characterization application 334, and a database 336. The IVUS console 310 is used to acquire RF backscattered data from a vascular structure. Specifically, a transducer 322 is attached to the end of the catheter 320 and used (as previously discussed) to acquire ultrasound data backscattered from vascular tissue. The backscattered data is then transmitted to the computing device 330 via the IVUS console 310. Once the backscattered data is received, the transfer-function application 332 is used (as previously discussed) to estimate the transfer function (H) and to calculate the response data (X). The response data (X) and histology data (e.g., as stored in the database 336) are then used by the characterization application 334 to characterize at least a portion of the vascular tissue (e.g., identifying tissue type, etc.).

It should be appreciated that the IVUS console 310 depicted herein is not limited to any particular type of IVUS console, and includes all ultrasound devices generally known to those skilled in the art (e.g., Boston Scientific Clearview Imaging System, etc.). It should also be appreciated that the database 336 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the transfer-function application 332 and the characterization application 334 may exist as a single application or as multiple applications (i.e., more than one), locally and/or remotely stored.

Referring back to FIG. 3, the characterization application 334 is adapted to receive response data (X), to determine parameters related thereto, and use parameters stored in the database 336 (i.e., histology data) to identify tissue type(s) or characterization(s) thereof. Specifically, prior to the acquisition of the response data (e.g., from the transfer-function application 332), parameters are stored in the database 336 and linked to characterization data. Once the response data is acquired, the characterization application 334 is used to identify at least one parameter associated (either directly or indirectly) with the response data. The identified parameters are then compared to the parameters stored in the database (i.e., histology data). If a match (either exactly or substantially) is found, the related region (i.e., at least a portion of the vascular tissue) is correlated to the tissue type stored in the database 336 (e.g., as linked to the matching parameter(s)).

It should be appreciated that each parameter stored in the database 336 may be associated with more than one tissue type or characterizations. For example, a first parameter may be common to multiple tissue types, thus requiring additional parameters to narrow the field. It should also be appreciated that a match may occur as long as the parameters fall within a range of properties for a particular tissue type found in the database 336. It should further be appreciated that the terms "tissue type" and "characterization," as these terms are used herein, include, but are not limited to, fibrous tissues, fibrolipidic tissues, calcified necrotic tissues, calcific tissues, collagen, cholesterol, thrombus, compositional structures (e.g., the lumen, the vessel wall, the medial-adventitial boundary, etc.) and all other identifiable characteristics generally known to those skilled in the art.

In one embodiment of the present invention, the characterization application 334 is adapted to identify parameters directly from the response data (X), which is in the time domain. In another embodiment of the present invention, the characterization application 334 is adapted to perform signal analysis (i.e., frequency analysis, etc.) on the response data (X) before the parameters are identified. In other words, for example, the response data (X) might be converted (or transformed) into the frequency domain before parameters are identified. In another embodiment of the present invention, the characterization application 334 is adapted to identify parameters from both the response data (X) and its frequency spectrum. This is because the response data, which is in the time domain, can be used to spatially identify certain frequencies (or parameters related thereto). For example, if a vascular structure comprises multiple tissue layers, corresponding backscattered data can be used to identify the location of these tissues and the related frequency spectrum can be used to identify tissue types (see e.g., FIGS. 2C and 2D). These concepts are discussed in more detail in U.S. Pat. No. 6,200,268 and patent application Ser. No. 10/647,971 (as previously identified)

It should be appreciated that, while certain embodiments have been described in terms of frequency transformation, the present invention is not so limited. Thus, alternate transformations (e.g., wavelet transformation, etc.) are within the spirit and scope of the present invention. It should also be appreciated that the term parameter, as that term is used herein, includes, but is not limited to maximum power, minimum power, frequencies at maximum and/or minimum power, y intercepts (estimated or actual), slope, mid-band fit, integrated backscatter and all parameters generally known to (or discernable by) those skilled in the art. It should be further appreciated that the response data may either be received and/or analyzed (e.g., to identify parameters) in real-time (e.g., while the catheter is in the patient) or after a period of delay.

In one embodiment of the present invention, the characterization application 334 is further adapted to display a reconstructed image of at least a portion of the interrogated vascular structure on a display (e.g., the IVUS console 310, a computing device display (not shown), etc.). In the image, each tissue type (or characterization) is distinguished by using gray-scales or colors (e.g., different colors correspond to different tissue types, etc.). Such a system makes different tissue types or characterizations easily identifiable.

Figure 4:
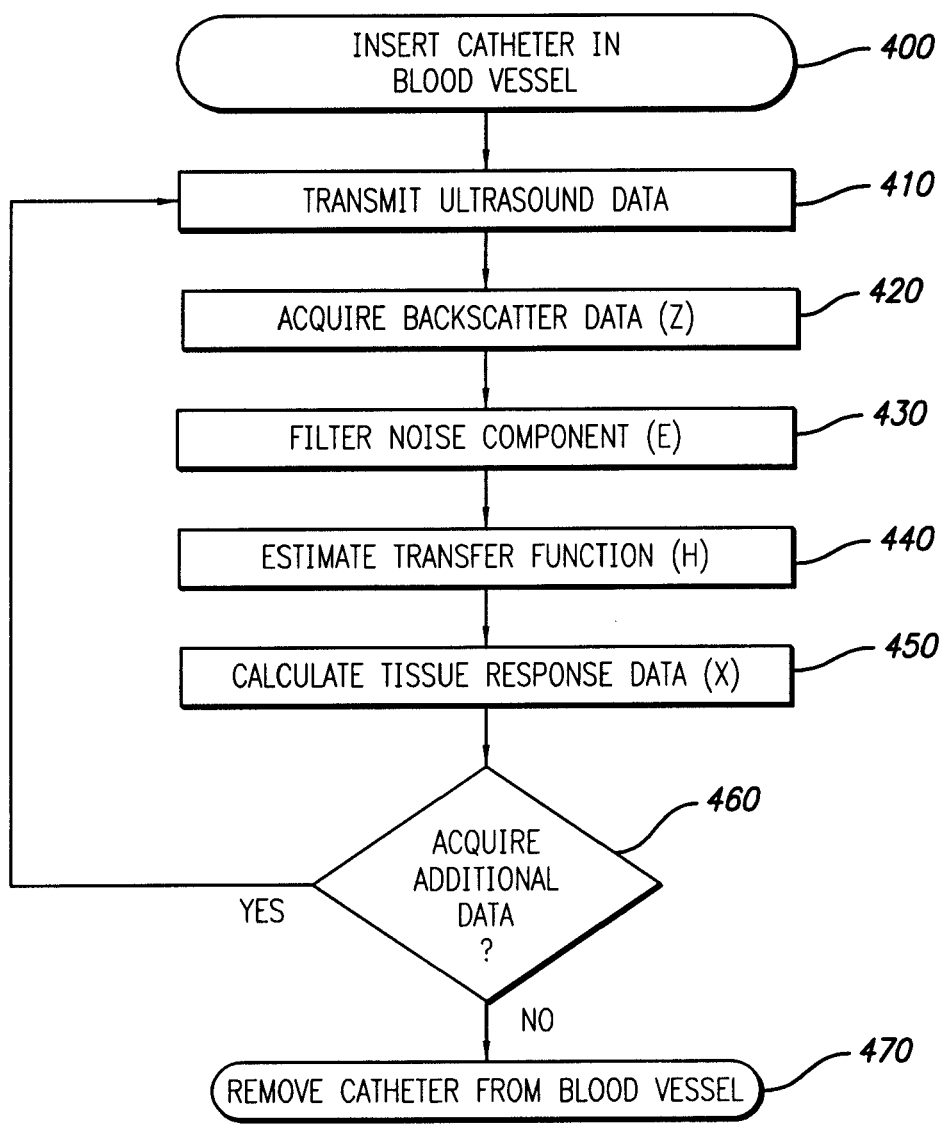
FIG. 4 illustrates a method of calculating ultrasound response data for vascular tissue.

One method of acquiring response data for vascular tissue is illustrated in FIG. 4. Specifically, at step 400, a catheter having at least one transducer is inserted into a vascular structure (e.g., blood vessel). The catheter is then used to transmit ultrasound data toward a tissue portion of the vascular structure (i.e., vascular tissue) at step 410. Ultrasound data backscattered from the vascular tissue (Z) is then acquired at step 420. At step 430, a noise component (E) of the backscattered ultrasound data (Z) is filtered (e.g., removed, reduced, etc.). At step 440, the backscattered ultrasound data (Z) is used to estimate the catheter's transfer function (H). In one embodiment of the present invention, this step is performed in real-time (e.g., while multiple sets of backscattered data are being acquired, while the catheter is in the vascular structure, etc.). At step 450, the estimated transfer function (H) is used to calculate response data for the vascular tissue (X). If additional data is to be acquired (i.e., step 460), then the process repeats (i.e., starting at step 410). If no more data is needed, then the catheter is removed from the vascular structure at step 470. It should be appreciated that the order in which these steps are presented is not intended to limit the present invention. Thus, for example, filtering the noise component (E) after the transfer function (H) is estimated is within the spirit and scope of the present invention.

Having thus described embodiments of a system and method of using ultrasound data backscattered from vascular tissue to estimate the transfer function of a catheter, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A system for acquiring ultrasound response data, comprising:
    a catheter including at least one transducer and adapted to transmit an ultrasound signal and to receive a backscatter of said ultrasound signal, the catheter being sized and shaped for maneuvering through a vascular structure such that the catheter is positionable at a first location for acquiring first backscattered ultrasound data from a first portion of the vascular structure; and a processing system in communication with the catheter, the processing system configured to:
  estimate a first transfer function of the catheter based on at least a portion of the first backscattered ultrasound data, the first transfer function being independent of the vascular structure; and
  calculate first ultrasound response data based on the first transfer function such that the first ultrasound response data is independent of ultrasound data modifications resulting from the catheter.

2. The system of claim 1, wherein the processing system is further configured to filter noise from the first backscattered ultrasound data.

3. The system of claim 1, wherein the processing system is configured to estimate the first transfer function using an iterative algorithm that is time-invariant over small intervals.

4. The system of claim 1, wherein the processing system is configured to estimate the first transfer function using an error-criteria algorithm and a least-squares-fit algorithm.

5. The system of claim 1, further comprising a display in communication with the processing system, the display configured to display images of the vascular structure based on imaging signals received from the processing system.

6. The system of claim 5, wherein the imaging signals are based on the first ultrasound response data.

7. The system of claim 1, wherein the processing system is further configured to:
  identify one or more parameters of the first ultrasound response data; and
  characterize a tissue type of the first portion of the vascular tissue based on the one or more parameters.

8. The system of claim 7, wherein the processing system identifies the one or more parameters of the first ultrasound response data by:
  transforming the first ultrasound response data from a time domain into a frequency domain; and
  identifying the one or more parameters from the frequency spectrum of the first ultrasound response data.

9. The system of claim 7, wherein at least one of the one or more parameters is selected from the group of parameters consisting of: maximum power, minimum power, frequency at maximum power, frequency at minimum power, y intercept, slope, mid-band fit, and integrated backscatter.

10. The system of claim 7, wherein the tissue type is selected from the group of tissue types consisting of: fibrous tissues, fibrolipidic tissues, calcified necrotic tissues, and calcific tissues.

11. The system of claim 7, further comprising a display in communication with the processing system, the display configured to display images of the vascular structure based on imaging signals received from the processing system.

12. The system of claim 11, wherein the images of the vascular structure have different colors for different tissue types.

13. The system of claim 1, wherein the catheter is positionable at a second location for acquiring second backscattered ultrasound data from a second portion of the vascular structure; and wherein the processing system is further configured to:
  estimate a second transfer function of the catheter based on at least a portion of the second backscattered ultrasound data, the second transfer function being independent of the vascular structure; and
  calculate second ultrasound response data based on the second transfer function such that the second ultrasound response data is independent of ultrasound data modifications resulting from the catheter.

14. A system for acquiring ultrasound response data, comprising:
  a catheter including at least one transducer and adapted to transmit an ultrasound signal and to receive a backscatter of said ultrasound signal, the catheter being sized and shaped for maneuvering through a vascular structure such that the catheter is positionable at a first location for acquiring first backscattered ultrasound data from a first portion of the vascular structure; and
  a processing system in communication with the catheter, the processing system configured to:
    estimate a first transfer function of the catheter based on at least a portion of the first backscattered ultrasound data; and
    calculate first ultrasound response data based on the first transfer function such that the first ultrasound response data is independent of ultrasound data modifications resulting from the catheter, the first transfer function describing data removed the first backscattered ultrasound data to calculate the first ultrasound response data.

15. The system of claim 14, wherein the processing system is further configured to filter noise from the first backscattered ultrasound data.

16. The system of claim 14, wherein the processing system is configured to estimate the first transfer function using an iterative algorithm that is time-invariant over small intervals.

17. The system of claim 14, wherein the processing system is configured to estimate the first transfer function using an error-criteria algorithm and a least-squares-fit algorithm.

18. The system of claim 14, further comprising a display in communication with the processing system, the display configured to display images of the vascular structure based on imaging signals received from the processing system.

19. The system of claim 18, wherein the imaging signals are based on the first ultrasound response data.

20. The system of claim 14, wherein the processing system is further configured to:
  identify one or more parameters of the first ultrasound response data; and
  characterize a tissue type of the first portion of the vascular tissue based on the one or more parameters.

21. The system of claim 20, wherein the processing system identifies the one or more parameters of the first ultrasound response data by:
  transforming the first ultrasound response data from a time domain into a frequency domain; and
  identifying the one or more parameters from the frequency spectrum of the first ultrasound response data.

22. The system of claim 20, wherein at least one of the one or more parameters is selected from the group of parameters consisting of: maximum power, minimum power, frequency at maximum power, frequency at minimum power, y intercept, slope, mid-band fit, and integrated backscatter.

23. The system of claim 20, wherein the tissue type is selected from the group of tissue types consisting of: fibrous tissues, fibrolipidic tissues, calcified necrotic tissues, and calcific tissues.

24. The system of claim 20, further comprising a display in communication with the processing system, the display configured to display images of the vascular structure based on imaging signals received from the processing system.

25. The system of claim 24, wherein the images of the vascular structure have different colors for different tissue types.

26. The system of claim 14, wherein the catheter is positionable at a second location for acquiring second backscattered ultrasound data from a second portion of the vascular structure; and wherein the processing system is further configured to:
    estimate a second transfer function of the catheter based on at least a portion of the second backscattered ultrasound data; and
    calculate second ultrasound response data based on the second transfer function such that the second ultrasound response data is independent of ultrasound data modifications resulting from the catheter, the second transfer function describing data removed the second backscattered ultrasound data to calculate the second ultrasound response data.

\* \* \* \* \*